United States Patent
Braun et al.

(10) Patent No.: US 9,980,851 B2
(45) Date of Patent: May 29, 2018

(54) INSTRUMENT FOR STIMULATING OR IRRITATING AND/OR ABRASIVELY TREATING AND/OR POLISHING A MEMBRANE OR SURFACE OR INNER SURFACE IN THE HUMAN OR ANIMAL EYE

(71) Applicant: GEUDER AG, Heidelberg (DE)

(72) Inventors: Norbert Braun, Meckesheim (DE); Boris V. Stanzel, Bonn (DE); Frank G. Holz, Bonn (DE); Ralf Brinken, Bonn (DE)

(73) Assignee: GEUDER AG, Heidelberg (DE)

( * ) Notice: Subject to any disclaimer, the term of this patent is extended or adjusted under 35 U.S.C. 154(b) by 112 days.

(21) Appl. No.: 14/649,354

(22) PCT Filed: Nov. 27, 2013

(86) PCT No.: PCT/DE2013/200320
§ 371 (c)(1),
(2) Date: Jun. 3, 2015

(87) PCT Pub. No.: WO2014/090244
PCT Pub. Date: Jun. 19, 2014

(65) Prior Publication Data
US 2015/0297406 A1 Oct. 22, 2015

(30) Foreign Application Priority Data

Dec. 13, 2012 (DE) .......................... 10 2012 223 076

(51) Int. Cl.
*A61B 17/32* (2006.01)
*A61F 9/007* (2006.01)
(Continued)

(52) U.S. Cl.
CPC .......... *A61F 9/00736* (2013.01); *A61B 17/32* (2013.01); *A61B 17/32056* (2013.01);
(Continued)

(58) Field of Classification Search
CPC ...... A61B 17/32056; A61B 17/320708; A61B 2017/320008; A61F 9/00736
(Continued)

(56) References Cited

U.S. PATENT DOCUMENTS

| 612,569 | A | * | 10/1898 | Moscrop | .......... A61B 17/32056 606/113 |
| 1,833,687 | A | * | 11/1931 | Neivert | .................. A61B 17/26 606/113 |

(Continued)

FOREIGN PATENT DOCUMENTS

| DE | 29819018 U1 | 3/1999 |
| DE | 19948349 A1 | 5/2001 |

(Continued)

OTHER PUBLICATIONS

Binder, S., et al., "Transplantation of the RPE in AMD", Progress Retinal Eye Research, 2007, 39 pages, Elsevier Ltd., UK.
(Continued)

*Primary Examiner* — Kathleen Holwerda
(74) *Attorney, Agent, or Firm* — Alston & Bird LLP

(57) ABSTRACT

The invention relates to an instrument for stimulating or irritating and/or abrasively treating and/or polishing a membrane or surface or inner surface in the human or animal eye, comprising a handle (1), which comprises an actuating element (2), and a probe (3), which adjoins the handle (1) and which is open at the free distal end, for introducing into the eye. The invention is characterized in that the probe (3) comprises a loop (4) in the interior, and the loop can be at least slightly pushed out of the probe (3) and pushed or (Continued)

pulled back into the probe (3) by means of the actuating element (2).

17 Claims, 4 Drawing Sheets

(51) Int. Cl.
    *A61B 17/3205*     (2006.01)
    *A61B 17/3207*     (2006.01)
    *A61L 31/02*     (2006.01)
    *A61L 31/04*     (2006.01)
    *A61L 31/14*     (2006.01)
    *A61B 17/30*     (2006.01)

(52) U.S. Cl.
    CPC .... *A61B 17/320708* (2013.01); *A61L 31/022* (2013.01); *A61L 31/04* (2013.01); *A61L 31/048* (2013.01); *A61L 31/14* (2013.01); *A61B 2017/305* (2013.01); *A61B 2017/320004* (2013.01); *A61B 2017/320008* (2013.01)

(58) Field of Classification Search
    USPC .......................... 606/107, 113, 161, 166, 170
    See application file for complete search history.

(56) References Cited

U.S. PATENT DOCUMENTS

| | | | |
|---|---|---|---|
| 5,112,339 A * | 5/1992 | Zelman | A61F 9/00745 |
| | | | 606/107 |
| 6,554,842 B2 * | 4/2003 | Heuser | A61B 17/221 |
| | | | 606/108 |
| 6,575,989 B1 | 6/2003 | Scheller et al. | |
| 6,860,894 B1 * | 3/2005 | Pittman | A61B 17/00234 |
| | | | 606/113 |
| 2005/0043756 A1 * | 2/2005 | Lavelle | A61B 17/221 |
| | | | 606/200 |
| 2005/0159648 A1 * | 7/2005 | Freed | A61B 17/32056 |
| | | | 600/159 |
| 2008/0183199 A1 * | 7/2008 | Attinger | A61F 9/00736 |
| | | | 606/161 |
| 2009/0054904 A1 * | 2/2009 | Holmen | A61B 17/320016 |
| | | | 606/107 |
| 2010/0312232 A1 | 12/2010 | Jia et al. | |
| 2015/0257927 A1 * | 9/2015 | Olson | A61F 9/00821 |
| | | | 606/107 |

FOREIGN PATENT DOCUMENTS

| | | |
|---|---|---|
| DE | 102010055870 A1 | 6/2012 |
| DE | 102011100371 A1 | 11/2012 |
| EP | 0967919 B1 | 10/2006 |
| WO | WO 2000/076403 A1 | 12/2000 |
| WO | WO 2011/097578 A1 | 8/2011 |
| WO | WO 2012/150289 A2 | 11/2012 |

OTHER PUBLICATIONS

International Searching Authority, International Search Report (ISR) and Written Opinion for International Application No. PCT/DE2013/200320, dated Apr. 2, 2014, 9 pages, European Patent Office, The Netherlands.

The International Bureau of WIPO, International Preliminary Report on Patentability (English translation of ISA's Written Opinion) for International Application No. PCT/DE2013/200320, dated Jun. 16, 2015, 5 pages, Switzerland.

\* cited by examiner

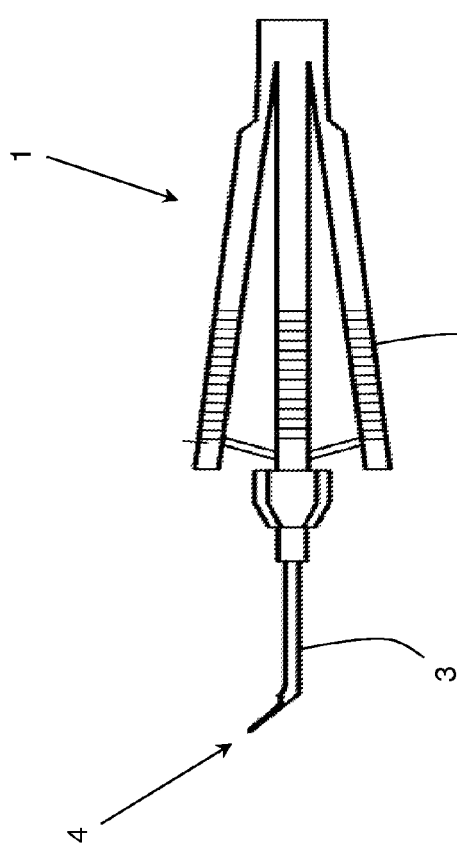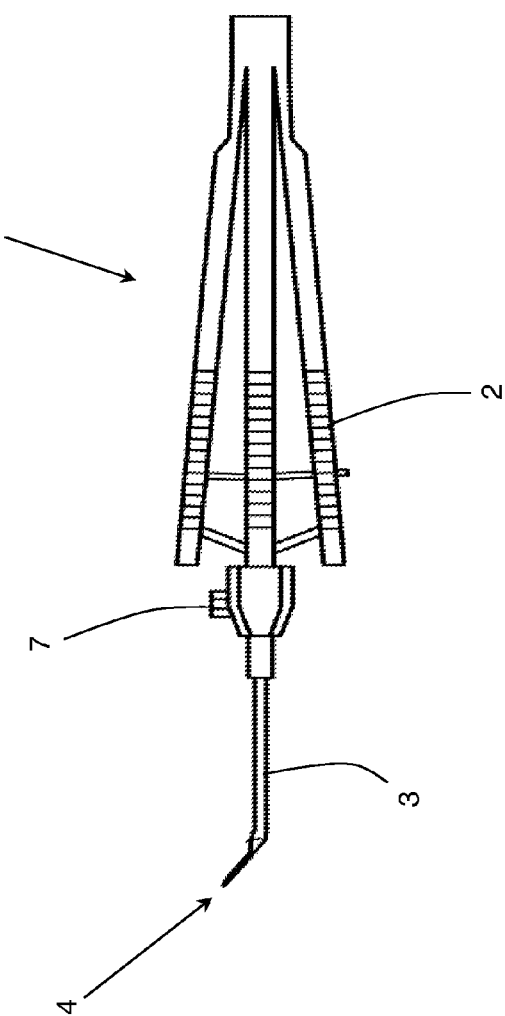

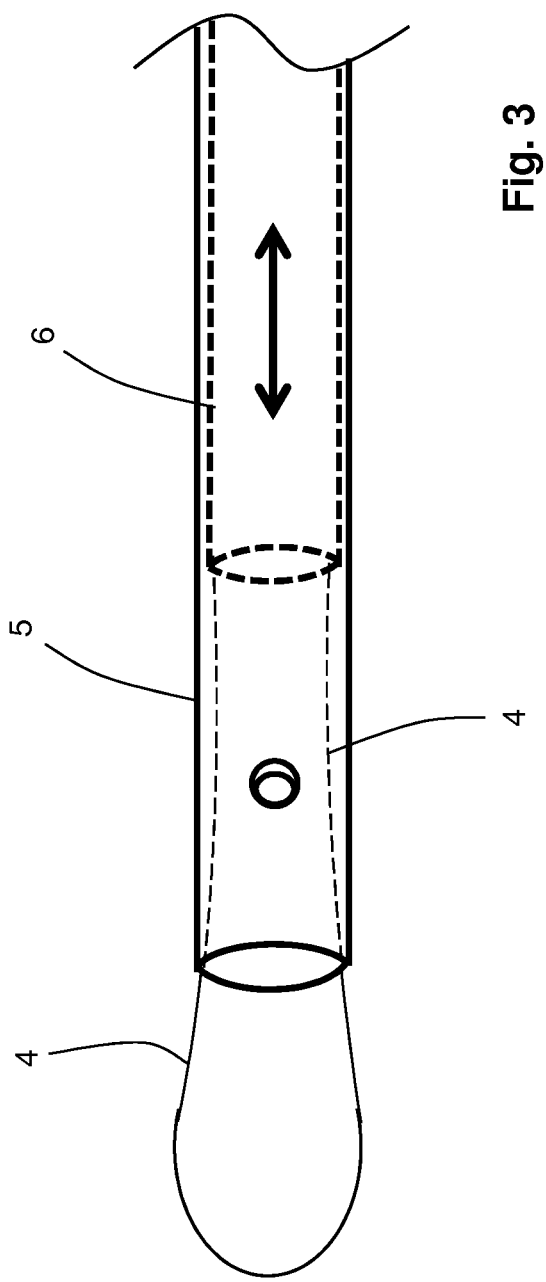

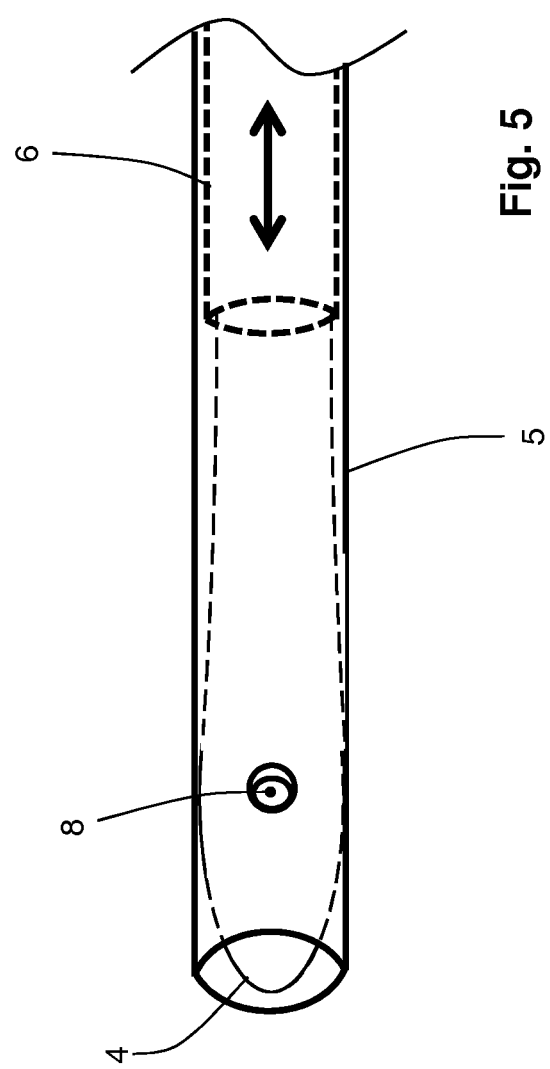

INSTRUMENT FOR STIMULATING OR IRRITATING AND/OR ABRASIVELY TREATING AND/OR POLISHING A MEMBRANE OR SURFACE OR INNER SURFACE IN THE HUMAN OR ANIMAL EYE

CROSS REFERENCE TO RELATED APPLICATIONS

This application is a national stage application, filed under 35 U.S.C. § 371, of International Application No. PCT/DE2013/200320, filed Nov. 27, 2013, which claims priority to German Application No. 10 2012 223 076.9, filed Dec. 13, 2012, the contents of which as are hereby incorporated by reference in their entirety.

BACKGROUND

Technical Field

The invention relates to an instrument that is designed for stimulating or more specifically irritating and/or for abrasively treating and/or polishing a membrane or surface or inner surface in the human or animal eye and that has a handle, enclosing an actuating element, and a probe, which adjoins the handle and is open on the free, distal end, for insertion into the eye.

The instrument under discussion here concerns an instrument for use in ophthalmic surgery, in particular, for the preparation of the subretinal insertion of an implant for the treatment of age-related macular degeneration (AMD). The replacement of functionally impaired, submacular RPE (retinal pigment epithelium) cells may be a treatment with a curative potential for advanced forms of AMD, i.e., to restore the homeostasis in the RPE and photoreceptor complex. Ultimately the objective is to provide the photoreceptors with a functional RBE [sic: RPE]. An overview of the procedure may be found in Binder S., Stanzel B. V., Krebs I., Glittenberg C. Transplantation of the RPE in AMD. Prog Retin Eye Res 2007; 26:516-554.

Description of Related Art

Instruments for inserting a subretinal implant are known, for example, from DE 10 2011 100 371 A1, DE 298 19 018 U1, EP 0 967 919 B1 and WO 00/76403 A1.

BRIEF SUMMARY

The invention is based on the following consideration:

Implanting RPE monolayer transplants on an intact RPE layer of a receiver can produce aberrant or unwanted signaling cascades. An intact RPE also represents a metabolic barrier for the transplant. As a result, AMD patients with dry intermediate or geographic atrophy with foveal thinning have, as potential candidates for the RPE removal, an intact RPE at the desired implantation site.

It is based on the assumption that an atraumatic removal of the host RPE can improve the metabolism of the RPE transplant by approaching the Bruch's membrane/the choriocapillaris complex. In addition, with this technique it is possible to create bases for anchoring strategies of the cell support material in the extracellular matrix. This approach allows aged, and possibly degenerated, cells of the patient to be replaced and position stabilized by means of a presumably healthy RPE transplant.

Silicon spatulas, coated with diamond dust, are known from practical application. However, during abrasive application these spatulas can cause damage in the retina and Bruch's membrane [BM].

A hydraulic RPE debridement, which is also known from practical application, can lead to RPE dispersion in the cavity of the vitreous body and thus, result in proliferative vitreoretinopathy. In addition, too strong a jet of liquid or too aggressive a manipulation in the subretinal space itself can cause significant damage to a photoreceptor.

An abrasive RPE ablation with a silicone or metal cannula leads to fissures in and damage to the BM and the choriocapillaris due to the direct propagation of the vectorial forces exerted by the surgeon's hand. An ethylenediaminetetraacetic acid [EDTA] assisted removal of the RPE opens the "tight junctions" of the RPE, as a result of which, the cell-to-cell adhesion may be loosened, but with little or no effect on the adhesion of the RPE to the BM. In addition, it has been proven that EDTA has photoreceptor toxicity, for which reason its use on the patient appears to be ruled out, according to the current level of knowledge.

The selective RPE destruction by means of a suitable laser leads to irreversible thermal damage in adjacent areas and is also cost intensive due to the equipment that is required.

Based on the methods known from practical application and the instruments that are used with said methods and taking into consideration the drawbacks associated with the use of such instruments, the object of the present invention is to provide an instrument for stimulating or more specifically irritating and/or abrasively treating and/or for polishing a membrane or surface or inner surface in the human or animal eye, where in this case said instrument exhibiting an extremely simple design enables an atraumatic removal of the RPE. In addition, the objective is for this instrument to lend itself to being capable of stimulating or more specifically irritating and abrasively treating or polishing, as needed, any membrane or surfaces in the eye and, in so doing, with low stress, in particular, with respect to the adjacent regions.

The above engineering object is achieved by means of an instrument according to patent claim 1, according to which such an instrument is characterized in that the probe comprises, in the interior, a loop, which can be pushed at least slightly out of the probe and can be pushed or pulled back into the probe by means of the actuating element.

The instrument according to the invention is a strictly mechanical instrument exhibiting a surprisingly simple design. This instrument has a handle with an actuating element and a probe, which adjoins the handle and is open on the distal end. Said probe is used for insertion into the eye, i.e. for insertion into the region, which is to be mechanically treated, or more specifically as far as to the surface/the membrane that is to be mechanically treated. The probe comprises in its interior, for example, in a channel that extends through the probe, a loop, which can be pushed at least slightly out of the probe and can be pushed or pulled back into the probe by means of the actuating element. When inserted into the eye, the loop is in the interior of the probe. Locally, i.e. in the inserted state in the eye, the loop can be moved out of the probe, as a result of which the loop develops the size and shape required for the processing. After completion of the operative procedure, the loop can be easily pushed back again into the probe, so that the probe can be safely pulled out of the eye.

The mechanism that is implemented here makes it feasible, for example, that only the loop has to be inserted into the subretinal space. This feature reduces the complexity of the operation.

The loop is advantageously a thin metal or plastic wire. A loop, which lends itself especially well, is one that is made of a crystalline stereoisomer of polypropylene. In the specific case as regards the loop, it can be a commercially available suture material, which is on the market under the trade name "PROLENE".

The loop is made extremely thin and may have a material diameter of about 0.06 to 0.07 mm. In the pushed-out state, as measured from the free end of the probe, the loop may have a length of 2 to 4 mm, preferably 3 mm. An inner diameter of 1 to 2 mm, preferably 1.6 mm, has demonstrated its worth in use.

In terms of structure it is also advantageous, if the probe comprises an outer guide tube and an inner tube, which bears the loop at the end, where in this case the inner tube can be displaced inside the guide tube by operating the actuating element. By sliding the loop-bearing inner tube, the loop can be moved out of the guide tube and moved into the guide tube, as a function of the direction of displacement. In other words, a simple actuating mechanism is provided here that moves the loop, which is attached to the inner tube, out of the guide tube and also back again into said guide tube by moving the inner tube.

The loop is attached in such an extremely sophisticated way to the free end of the guide tube and in the retracted state has such a mechanical prestress that it gradually widens when moved out of the guide tube.

In order to handle the instrument with ease, it is also advantageous if the respective state of the loop, for example, the extended state, can be secured by fixing the inner tube relative to the guide tube by means of a clamping mechanism, preferably by means of a set screw. This feature guarantees a safe handling of the instrument.

Moreover, the handling of the instrument is aided by the fact that a front region of the probe is bent down at least slightly relative to the longitudinal axis of the probe, preferably by about 15°. At such a tilt angle the RPE surface can be processed, for example, in a "flat layer" by applying the elastic properties and curvature of the loop material. In addition, the instrument according to the invention ensures a significant damping of uncontrolled or too "rough" movements of the surgeon. A smooth surface of the loop also allows the loop to slide easily and smoothly on the respective surface/membrane with a low probability of tissue laceration.

An additional mechanical design of the probe or more specifically the guide tube is an oval or flattened off cross-section in the region of the free end. In the context of such a design the thin loop may lie in the oval or flattened off tube in such a way that said loop is simply folded and retracted. After inserting the probe into the eye, the loop can be moved out in an ideal way until the diameter that is required for treatment is reached.

Another sophisticated measure is the precautionary measure of providing at least one opening in the guide tube, close to the free end. Such an opening is used to balance the pressure, i.e. to avoid situations of negative pressure/positive pressure in the region of the probe inside the eye. Unrestricted pressure equalization is possible. The passage can extend transversely to the longitudinal direction of the guide tube.

Moreover, it should also be noted that the instrument according to the invention can be made in its entirety of stainless steel. Similarly it is also conceivable to make the components of the instrument totally or at least partially of a synthetic plastic material, for example, in the context of an instrument that is intended for a single use.

As already stated above, the instrument according to the invention is a strictly mechanically acting instrument that has an extremely simple design and is very easy to handle.

Such an instrument can also be used for epiretinal membrane peeling in the context of macular surgery. For this purpose a surface modification of the loop could be made, for example, by coating the actual loop material with nano fibers or micro/nano particles, in order to intensify the effect of the loop with respect to the abrasive effect.

It is also conceivable to use the inventive instrument for mobilizing, as a general principle, the surfaces or more specifically the membranes: in other words, in order to put there the mobilization-promoting stimuli. Basically any and all applications of the inventive instrument in the eye are conceivable, so that at least one stimulation of the cells takes place. Therefore, the treatment of scars, in particular, the polishing at or on the inner surface of the lens capsule, is also possible. Last, but not least, owing to the damping character of the instrument in relation to the transmission of forces a universal and, at the same time, safe application in the eye is possible. The loop's effect over a wide area when it expands minimizes the risk of forces acting on specific points, meaning the inventive instrument acts gently, in contrast to the use of a spatula, rubber, etc.; and in an analogous manner a large area or more specifically a large volume can be achieved.

At this point there are a number of possibilities for embodying and further developing the teaching of the present invention in an advantageous way. For this purpose, reference is made, on the one hand, to the patent claims subordinate to patent claim 1 and, on the other hand, to the following explanation of the preferred exemplary embodiments of the invention with reference on the drawings. In conjunction with the explanation of the preferred exemplary embodiments of the invention with reference to the drawings, the generally preferred embodiments and further developments of the teaching are also explained. The drawings show

BRIEF DESCRIPTION OF THE FIGURES

FIG. 1 in a schematic view an exemplary embodiment of an inventive instrument provided with a bent probe;

FIG. 2 in a schematic view another exemplary embodiment of an inventive instrument provided with a clamping mechanism for fixing a working position; and FIGS. 3 to 5 in an enlarged view the distal end of the probe provided with the extended loop in a plan view (FIG. 3), with the extended loop in a side view (FIG. 4) and with the retracted loop in a plan view (FIG. 5), where in this case the probe is bent down and has a passage for pressure equalization.

DETAILED DESCRIPTION OF VARIOUS EMBODIMENTS

Figure 4:
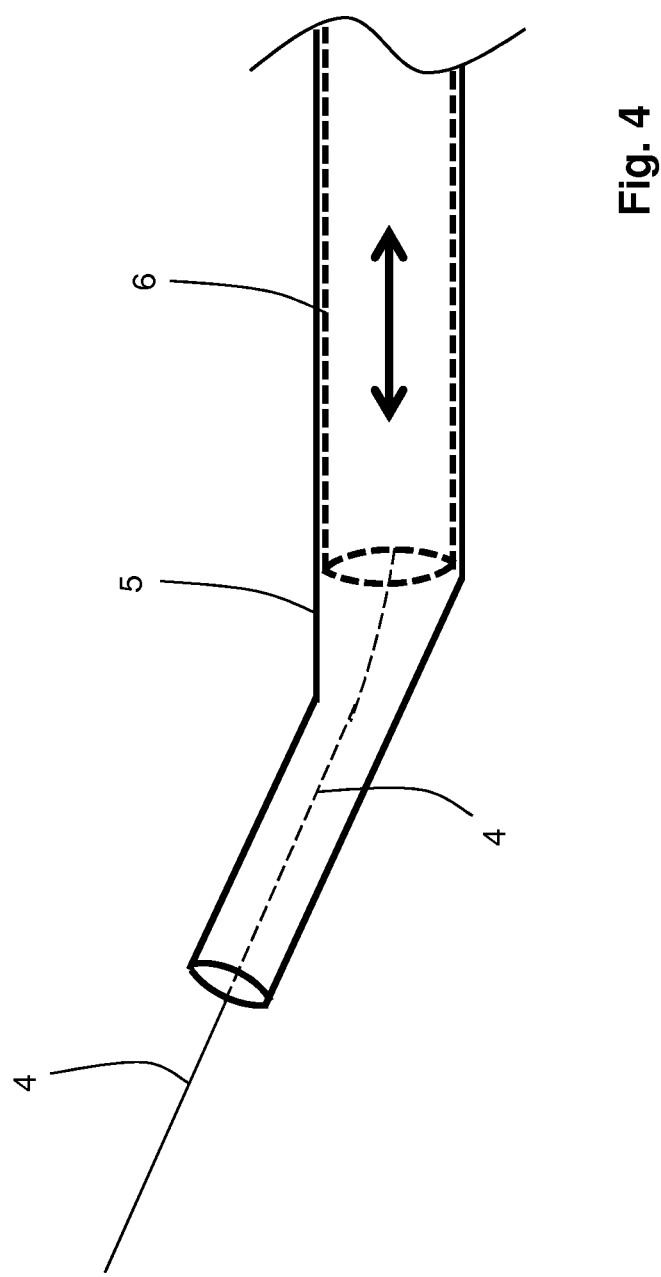

FIGS. 1 and 2 show in a schematic view two exemplary embodiments of an inventive instrument for stimulating or more specifically irritating and/or for abrasively treating and/or polishing the membrane or surface or inner surface in the human or animal eye. The instrument comprises a handle 1 and an actuating element 2, which is assigned to a handle 1, where in this case said actuating element is an integral part of the handle 1.

Adjoining the handle 1 is a probe 3, which is open at the free, distal end. The probe 3 is used for insertion into the eye.

According to the invention, the probe 3 comprises, in the interior, a loop 4, which can be pushed at least slightly out of the probe 3 and can be pushed or pulled back into the probe 3 by means of the actuating element 2. The loop is shown in the respective states in FIGS. 3, 4 and 5.

The loop 4 may be a metal or plastic wire, here in the specific case, a wire made of a crystalline stereoisomer of polypropylene.

The loop 4 has a diameter in the range of 0.06 to 0.07 mm. In the extended state the loop 4 is about 3 mm long and has an internal diameter of about 1.6 mm. As a result, a sufficiently large working area is guaranteed.

The probe 3 comprises an outer guide tube 5 and an inner tube 6, which bears the loop 4 on its end, where in this case the inner tube 6 can be displaced inside the guide tube 5 by actuating the actuating element 2. This displacement allows the loop 4 to be moved out of the guide tube 5 and into the guide tube 5.

According to the drawing in FIG. 2, a clamping mechanism 7 is provided in the form of a set screw, which makes it possible to fix the respective position of the loop 4.

Finally FIGS. 3 and 5 show the precautionary measure of providing a passage 8, which extends transversely to the longitudinal axis of the guide tube 5 and which is used to equalize the pressure, i.e. to avoid a negative pressure/positive pressure in the working region of the probe 3.

With regard to other features that cannot be derived from the figures, reference is made to the general part of the specification and the appended patent claims, in order to avoid repetition.

Finally it must be explicitly pointed out that the above-described exemplary embodiments of the instrument according to the invention serve only to explain the claimed teaching, but do not limit this teaching to the embodiments that are presented only for illustrative purposes.

LIST OF REFERENCE NUMERALS

1 Handle
2 Actuating Element
3 Probe
4 Loop
5 Outer Guide Tube
6 Inner Tube
7 Clamping Mechanism, Set Screw
8 Passage

The invention claimed is:

1. An instrument for stimulating or irritating and/or for abrasively treating and/or polishing a membrane or surface or inner surface in a human or animal eye, said instrument comprising:
   a handle (1) comprising an actuating element (2), and
   a probe (3), which adjoins the handle (1) and is open on a free, distal end, for insertion into the eye,
   wherein:
      the probe (3) comprises, in an interior, a loop (4), which can be pushed at least slightly out of the probe (3) and can be pushed or pulled back into the probe (3) by means of the actuating element (2),
      the probe (3) comprises an outer guide tube (5) and an inner guide tube (6), which directly bears the loop (4) at a distal end of the inner guide tube (6), and
      at least one passage (8), which is used for pressure equalization, is formed in the outer guide tube (5), close to the free, distal end of the probe (3), such that the distal end of the inner guide tube (6) remains proximal of the passage (8) when the loop (4) is in a fully extended position out of the probe (3).

2. The instrument, as claimed in claim 1, wherein the loop (4) is designed as a thin metal or plastic wire.

3. The instrument, as claimed in claim 1, wherein the loop (4) is made of a crystalline stereoisomer of polypropylene.

4. The instrument, as claimed in claim 1, wherein the loop (4) has a material diameter of about 0.06 to 0.07 mm.

5. The instrument, as claimed in claim 1, wherein starting from the free, distal end of the probe (3) the loop (4) in a pushed-out state has a length of 2 to 4 mm, and an inside diameter of 1 to 2 mm.

6. The instrument, as claimed in claim 1, wherein starting from the free, distal end of the probe (3) the loop (4) in a pushed-out state has a length of 3 mm, and an inside diameter of 1.6 mm.

7. The instrument, as claimed in claim 1, wherein the inner guide tube (6) can be displaced inside the outer guide tube (5) by operating the actuating element (2), as a result of which the loop (4) can be moved out of the outer guide tube (5) and moved into the outer guide tube (5).

8. The instrument, as claimed in claim 7, wherein the loop (4) is attached in such a way to a free end of the outer guide tube (5) and in a retracted state has such a mechanical pre-stress that it gradually widens when pushed out of the outer guide tube (5).

9. The instrument, as claimed in claim 7, wherein a respective state of the loop (4) can be secured by fixing the inner guide tube (6) relative to the outer guide tube (5) via a clamping mechanism (7).

10. The instrument, as claimed in claim 7, wherein a respective state of the loop (4) can be secured by fixing the inner guide tube (6) relative to the outer guide tube (5) via a set screw.

11. The instrument, as claimed in claim 1, wherein a front region of the probe (3) is bent down at an angle relative to the longitudinal axis of the probe (3).

12. The instrument, as claimed in claim 1, wherein a front region of the probe (3) is bent down 15° relative to the longitudinal axis of the probe (3).

13. The instrument, as claimed in claim 1, wherein the probe (3) has an oval or flattened off cross section in a region of the free, distal end of said probe.

14. The instrument, as claimed in claim 1, wherein the outer guide tube (5) has an oval or flattened off cross section in a region of a free end of the outer guide tube (5).

15. The instrument, as claimed in claim 1, wherein the at least one passage (8) extends more or less transversely to the longitudinal axis of the outer guide tube (5).

16. The instrument, as claimed in claim 1, wherein at least one of the handle, the actuating element, the probe, and the loop are made of at least one of stainless steel or a synthetic plastic material.

17. An instrument for stimulating or irritating and/or for abrasively treating and/or polishing a membrane or surface or inner surface in a human or animal eye, said instrument comprising:
   a handle (1) comprising an actuating element (2), and
   a probe (3), which adjoins the handle (1) and is open on a free, distal end, for insertion into the eye,
   wherein:
      the probe (3) comprises, in an interior, a loop (4), which can be pushed at least slightly out of the probe (3) and can be pushed or pulled back into the probe (3) by means of the actuating element (2),
      the probe (3) comprises an outer guide tube (5) and an inner guide tube (6), which directly bears the loop (4) at a distal end of the inner guide tube (6),
      at least one passage (8), which is used for pressure equalization, is formed in the outer guide tube (5), close to the free, distal end of the probe (3), such that the distal end of the inner guide tube (6) remains proximal of the passage (8) when the loop (4) is pushed out of the probe (3), and the at least one passage (8) extends, along an entire length of the at least one passage (8), in a direction transverse to the longitudinal axis of the outer guide tube (5).

\* \* \* \* \*